United States Patent [19]

Zfira

[11] Patent Number: 5,157,968
[45] Date of Patent: Oct. 27, 1992

[54] APPARATUS FOR MEASURING THE SPECIFIC GRAVITY, WEIGHT, LEVEL, AND/OR VOLUME OF A LIQUID IN A CONTAINER

[76] Inventor: Uri Zfira, 15 241, Kfar Tavor, Israel

[21] Appl. No.: 659,666

[22] Filed: Feb. 25, 1991

[30] Foreign Application Priority Data

Feb. 27, 1990 [IL] Israel ......................................... 93545

[51] Int. Cl.⁵ ...................... G01F 22/00; G01F 23/60; G01N 9/10
[52] U.S. Cl. ........................................ 73/149; 73/309; 73/433
[58] Field of Search ................... 73/149, 309, 319, 433

[56] References Cited

U.S. PATENT DOCUMENTS

| | | | |
|---|---|---|---|
| 2,038,273 | 4/1936 | Eynon | 73/309 |
| 3,527,096 | 9/1970 | Cohn et al. | 73/309 |
| 4,244,218 | 1/1981 | Wohrl | 73/309 |
| 4,813,275 | 3/1989 | Castor | 73/309 X |

FOREIGN PATENT DOCUMENTS

| | | | |
|---|---|---|---|
| 344973 | 12/1921 | Fed. Rep. of Germany | 73/309 |
| 279630 | 11/1971 | U.S.S.R. | 73/309 |
| 669199 | 6/1979 | U.S.S.R. | 73/309 |

Primary Examiner—Hezron E. Williams
Assistant Examiner—Joseph W. Roskos
Attorney, Agent, or Firm—Benjamin J. Barish

[57] ABSTRACT

Apparatus for measuring the specific gravity, weight, level, and/or volume of a liquid in a container includes two load cells supported at the upper end of the container, a first body of known cross-sectional area extending through the interior of the container supported in suspension by one load cell, and a second body of known volume extending through the interior of the container and supported in suspension by the other load cell.

17 Claims, 1 Drawing Sheet

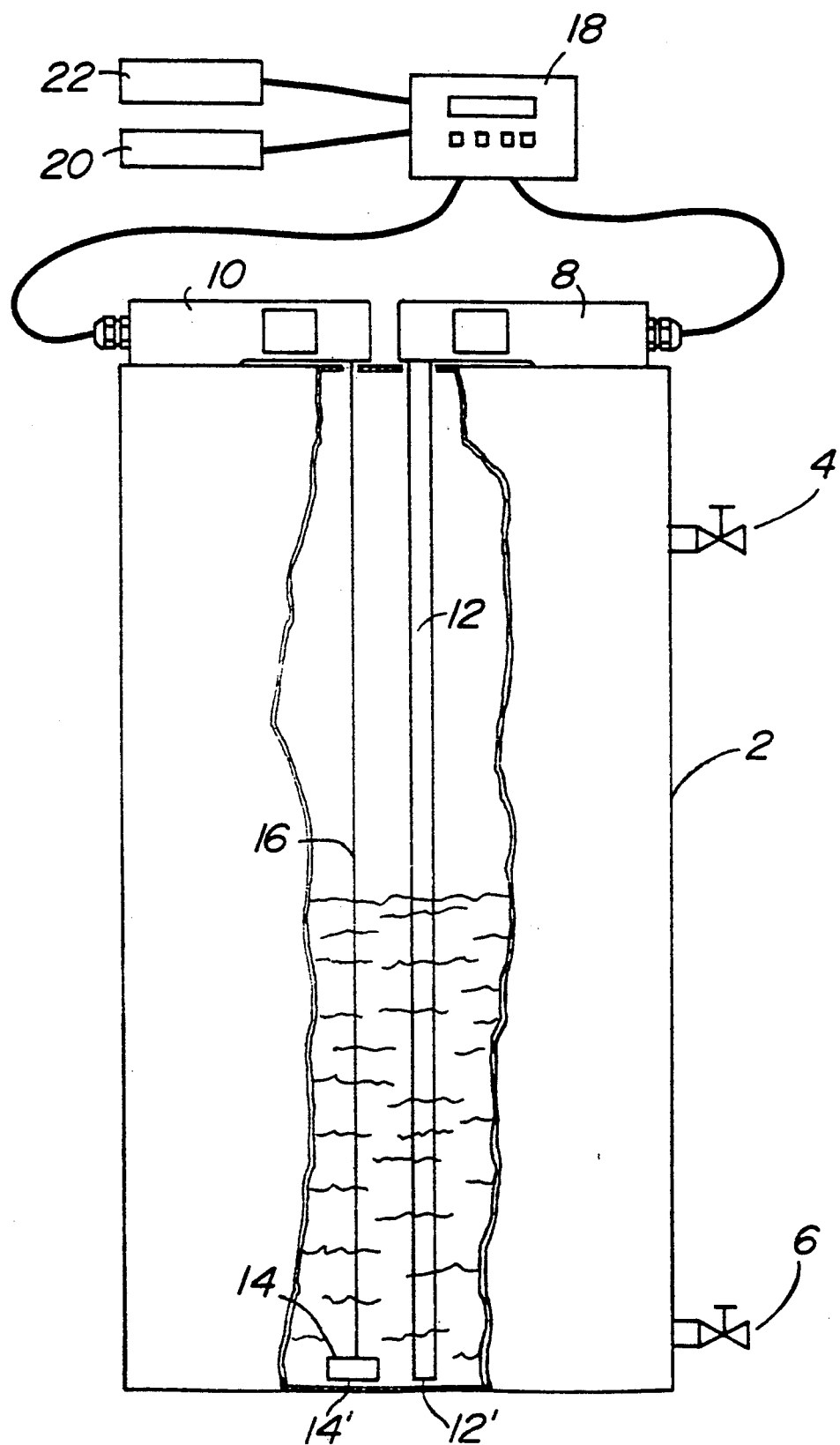

APPARATUS FOR MEASURING THE SPECIFIC GRAVITY, WEIGHT, LEVEL, AND/OR VOLUME OF A LIQUID IN A CONTAINER

BACKGROUND OF THE INVENTION

The present invention relates to liquid measuring apparatus, and particularly to apparatus for measuring the specific gravity, weight, level, and/or volume of a liquid in a container.

Many systems are known for making various measurements of liquids within containers, including systems which weigh the liquid together with its container of known weight or together with a container of both known weight and known volume, systems which measure volume or liquid level by the use of a float, etc. However, the known systems are usually relatively complicated and/or are limited as to the types of liquid measurements by which can be conveniently made.

OBJECTS AND BRIEF SUMMARY OF THE INVENTION

An object of the present invention is to provide a simple and efficient apparatus which may be used for measuring the specific gravity, weight, level, and/or volume of a liquid in a container.

An object of a preferred embodiment of the invention is to provide such apparatus which can monitor these measurements of a liquid in a continuous and real-time manner as liquid is introduced and/or removed from the container.

According to the present invention, there is provided apparatus for measuring the specific gravity, weight, level, and/or volume of a liquid in a container of known cross-sectional area, comprising: a first weight measuring device at the upper end of the container; a first body, of known cross-sectional area, extending through the interior of the container with the upper end of the body supported in suspension by the first weight measuring device, and the lower end of the body clear of the container bottom; a second weight measuring device at the upper end of the container; and a second body, of known volume, disposed within the container and supported in suspension by the second weight measuring device and clear of the container bottom. The second body is of a short length and is disposed near the bottom of the container such that it would normally be completely submerged by the liquid in the container. The first body is of a longer length such that it would normally be only partially submerged by the liquid in the container.

According to further features in a preferred embodiment of the invention described below, the first body is a rod of uniform cylindrical configuration and of known diameter, and is supported in suspension with its lower end at a small clearance from the container bottom; in addition, the second body, of known volume, is also supported in suspension with a small clearance from the container bottom.

According to further features in the described preferred embodiment, the first and second weight measuring devices are force transducers, such as load cells, which convert mechanical force to electrical signals. The apparatus further includes computer means for receiving the outputs of the first and second force transducers and for computing the specific gravity, weight, level, and/or volume of the liquid in the container.

It will thus be seen that apparatus constructed in accordance with the foregoing features provides a simple, efficient and inexpensive way of measuring the above parameters of a liquid in a container.

Further features and advantages of the invention will be apparent from the description below.

BRIEF DESCRIPTION OF DRAWING

The invention is herein described, somewhat schematically and by way of example only, with reference to the accompanying single figure of drawings illustrating one form of apparatus constructed in accordance with the present invention.

DESCRIPTION OF A PREFERRED EMBODIMENT

The apparatus illustrated in the drawing comprises a container, generally designated 2, having an inlet 4 at its upper end for introducing liquid into the container, and an outlet 6 at its lower end for removing liquid from the container. Container 2 is preferably of cylindrical configuration having a known diameter, and therefore a known cross-sectional area.

Mounted at the upper end of the container 2 are two weight measuring devices 8, 10. Preferably, both devices are force transducers, e.g., load cells, which convert mechanical force to electrical signals.

A first body 12 is supported in suspension by load cell 8. Body 12 is of known cross-sectional area and extends through the interior of container 2. The upper end of body 12 is fixed to load cell 8, and its lower end is spaced from the container bottom by a small clearance 12'. Body 12 is preferably a rod of uniform cylindrical configuration and of known diameter. It is preferably made of a metal which is resistant to the liquid to be introduced into container 2, and which has a higher specific gravity than that liquid.

Container 2 includes a second body 14 supported in suspension from load cell 10. In this case, body 14 is of known volume and is supported in suspension by a wire or cord 16, with the bottom of the body 14 spaced from the bottom of container 2 at a small clearance, as shown at 14'.

As can be seen from the drawing, body 14 is of a short length and is disposed near the bottom of the container 2 such that it would normally be completely submerged by the liquid in the container. Body 12, however, is of a longer length such that it would normally be only partially submerged by the liquid in the container.

The two load cells 8, 10 are connected to a microprocessor 18. Microprocessor 18 includes a computer which computes, from the information outputted by the load cells 8, 10 in a manner to be described more particularly below, the specific gravity, weight, level, and/or volume of the liquid within container 2 continuously or at any desired time. These measurements are displayed in a monitor unit 20 and/or printed out in a printer unit 22, both connected to the microprocessor 18.

The apparatus illustrated in the drawing is used in the following manner:

While container 2 is empty of liquid, the two load cells 8, 10 may be preset to provide a "0" reading in the monitor unit 20. Accordingly, when liquid is introduced into the container, these load cells will provide a measurement of the buoyant force applied by the liquid to the two bodies 12 and 14 supported in suspension from the two load cells 8, 10, respectively.

Since the cross-sectional area of container 2, the cross-sectional area of body 12, and the volume of body 14, are all known, the buoyant forces measured by the two load cells 8, 10, will enable the computer within microprocessor 18 to compute the specific gravity, weight, level, and/or volume of the liquid within the container 2 in the following manner:

First, the specific gravity (SG) of the liquid within the container may be computed as follows:

$$SG = \frac{BF_{10}}{V_{14}}$$

wherein: $BF_{10}$ is the buoyant force measured by load cell 10; and $V_{14}$ is the known volume of body 14.

The weight (W) of the liquid in the container may be computed as follows:

$$W = \frac{BF_8 \cdot A_2}{A_{12}}$$

wherein: $BF_8$ is the buoyant force measured by load cell 10; $A_2$ is the cross-sectional area of the container 2; and $A_{12}$ is the cross-sectional area of body 12.

The level L of the liquid within the container may be computed as follows:

$$L = \frac{BF_8}{A_{12} \cdot SG}$$

The above measurement of the liquid level (L) assumes that the clearance 12' of body 12 at the bottom of the container is negligible; otherwise, this clearance should be added to the computed value of $L_1$.

The volume of the liquid ($V_2$) within container 2 may be computed as follows:

$$V_2 = \frac{W}{SG}$$

While the invention has been described with respect to one preferred embodiment, it will be appreciated that many variations, modifications and other applications of the invention may be made.

What is claimed is:

1. Apparatus for measuring the specific gravity, weight, level, and/or volume of a liquid in a container of known cross-sectional area, comprising:
   a first weight measuring device at the upper end of the container;
   a first body, of known cross-sectional area, extending through the interior of the container with the upper end of the body supported in suspension by said first weight measuring device, and the lower end of the body clear of the container bottom;
   a second weight measuring device at the upper end of the container;
   and a second body, of known volume, disposed within the container and supported in suspension by said second weight measuring device and clear of the container bottom;
   said second body being of a short length and disposed near the bottom of the container such that it would normally be completely submerged by the liquid in the container;
   said first body being of a longer length such that it would normally be only partially submerged by the liquid in the container.

2. The apparatus according to claim 1, wherein said first body is a rod of uniform configuration.

3. The apparatus according to claim 1, wherein said first body is supported in suspension with its lower end at a small clearance from the container bottom.

4. The apparatus according to claim 1, wherein said second body is supported in suspension with its lower end at a small clearance from the container bottom.

5. The apparatus according to claim 1, wherein said first and second weight measuring devices are force transducers which convert mechanical force to electrical signals.

6. The apparatus according to claim 5, wherein said force transducers are load cells.

7. The apparatus according to claim 1, further including computer means for receiving the outputs of said first and second weight measuring devices and for computing the specific gravity, weight, level, and/or volume of the liquid in the container.

8. The apparatus according to claim 7, wherein said container includes an inlet for introducing the liquid into the container, and an outlet for removing liquid from the container; said computer continuously computing the specific gravity, weight, level, and/or volume of the liquid in the container.

9. The apparatus according to claim 8, wherein said computer further includes a monitor for displaying the computed specific gravity, weight, level, and/or volume of the liquid in the container at any particular time.

10. Apparatus for measuring the specific gravity, weight, level, and/or volume of a liquid in a container, comprising:
    first and second force transducers supported at the upper end of the container for converting mechanical force to electrical signals;
    a first body, of known cross-sectional area, extending through the interior of the container with the upper end of the body supported in suspension by said first force transducer, and the lower end of the body clear of the container bottom;
    and a second body, of known volume, extending through the interior of the container and supported in suspension by said second force transducer, with the lower end of the second body clear of the container bottom;
    said second body being of a short length and disposed near the bottom of the container such that it would normally be completely submerged by the liquid in the container;
    said first body being of a longer length such that it would normally be only partially submerged by the liquid in the container.

11. The apparatus according to claim 10, wherein said container is of known cross-sectional area.

12. The apparatus according to claim 11, wherein said first body is a rod of uniform cross-section and is supported in suspension with its lower end at a small clearance from the container bottom.

13. The apparatus according to claim 11, wherein said second body is supported in suspension from said second force transducer at a small clearance from the container bottom.

14. The apparatus according to claim 11, wherein said force transducers are load cells.

15. The apparatus according to claim 11, further including computer means for receiving the outputs of said first and second force transducers and for computing the specific gravity, weight, level, and/or volume of the liquid in the container.

16. The apparatus according to claim 15, wherein said container includes an inlet for introducing the liquid into the container, and an outlet for removing liquid from the container, said computer continuously computing the specific gravity, weight, level, and/or volume of the liquid in the container at any particular instant.

17. The apparatus according to claim 16, wherein said computer further includes a monitor for displaying the computed specific gravity, weight, level, and/or volume of the liquid in the container at any particular instant.

* * * * *